US00PP20823P2

(12) United States Plant Patent
Kanaya

(10) Patent No.: US PP20,823 P2
(45) Date of Patent: Mar. 9, 2010

(54) ***CALIBRACHOA* PLANT NAMED 'SUNBELREMO'**

(50) Latin Name: *Calibrachoa sp.*
Varietal Denomination: Sunbelremo

(75) Inventor: Takeshi Kanaya, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/313,675

(22) Filed: Nov. 21, 2008

(51) Int. Cl.
*A01H 5/00* (2006.01)

(52) U.S. Cl. ..... Plt./413

(58) Field of Classification Search ..... Plt./413
See application file for complete search history.

(56) References Cited

U.S. PATENT DOCUMENTS

PP11,558 P * 10/2000 Murakami ..... Plt./356

PP17,256 P2 * 12/2006 Pierce ..... Plt./413

OTHER PUBLICATIONS

UPOV ROM GTITM Computer Database, GTI Jouve Retrieval Software 2009/03 Citation for 'Sunbelremo'.*

Canadian Food Inspection Agency, Plant Varieties Journal No. 67 (Apr. 2008) see esp. p. 17.*

* cited by examiner

*Primary Examiner*—Wendy C Haas
(74) *Attorney, Agent, or Firm*—C. A. Whealy

(57) ABSTRACT

A new and distinct cultivar of *Calibrachoa* plant named 'Sunbelremo', characterized by its upright and mounding plant habit; vigorous growth habit; freely branching and flowering plant habit; long flowering period; medium-sized lemon yellow-colored flowers; and good garden performance.

1 Drawing Sheet

Botanical designation: *Calibrachoa* sp.
Cultivar denomination: 'Sunbelremo'.

BACKGROUND OF THE INVENTION

The present invention relates to a new and distinct cultivar of *Calibrachoa* plant, botanically known as *Calibrachoa* sp. and hereinafter referred to by the name 'Sunbelremo'.

The new *Calibrachoa* plant is a product of a planned breeding program conducted by the Inventor in Higashiomi, Shiga, Japan. The objective of the breeding program is to develop new mounding and freely-branching *Calibrachoa* cultivars with attractive and unique flower coloration.

The new *Calibrachoa* plant originated from a cross-pollination conducted by the Inventor in Higashiomi, Shiga, Japan in April, 2004 of a proprietary selection of *Calibrachoa* sp. identified as code number S39, not patented, as the female, or seed, parent with a proprietary selection of *Calibrachoa* sp. identified as code number YS5, not patented, as the male, or pollen, parent. The new *Calibrachoa* was discovered and selected by the Inventor as a single flowering plant from within the progeny of the stated cross-pollination in a controlled greenhouse environment in Higashiomi, Shiga, Japan in September, 2005.

Asexual reproduction of the new *Calibrachoa* plant by vegetative cuttings in a controlled greenhouse environment in Higashiomi, Shiga, Japan since October, 2005, has shown that the unique features of this new *Calibrachoa* plant are stable and reproduced true to type in successive generations.

SUMMARY OF THE INVENTION

Plants of the new *Calibrachoa* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunbelremo'. These characteristics in combination distinguish 'Sunbelremo' as a new and distinct cultivar of *Calibrachoa:*

1. Upright and mounding plant habit.
2. Vigorous growth habit.
3. Freely branching and flowering plant habit.
4. Long flowering period.
5. Medium-sized lemon yellow-colored flowers.
6. Good garden performance.

Plants of the new *Calibrachoa* can be compared to plants of the female parent selection. Plants of the new *Calibrachoa* differ from plants of the female parent selection in the following characteristics:

1. Plants of the new *Calibrachoa* are shorter than plants of the female parent selection.
2. Plants of the new *Calibrachoa* are more freely branching than plants of the female parent selection.

Plants of the new *Calibrachoa* can be compared to plants of the male parent selection. Plants of the new *Calibrachoa* differ from plants of the male parent selection in the following characteristics:

1. Plants of the new *Calibrachoa* are shorter than plants of the male parent selection.
2. Plants of the new *Calibrachoa* are more freely branching than plants of the male parent selection.
3. Plants of the new *Calibrachoa* and the male parent selection differ in flower color as plants of the male parent selection have red purple-colored flowers.

Plants of the new *Calibrachoa* can also be compared to plants of 'Sunbelki', disclosed in U.S. Plant Pat. No. 11,558. In side-by-side comparisons conducted in Higashiomi, Shiga, Japan, plants of the new *Calibrachoa* and 'Sunbelki' differed primarily in the following characteristics:

1. Plants of the new *Calibrachoa* were larger than plants of 'Sunbelki'.
2. Plants of the new *Calibrachoa* were more mounding than and not as spreading than plants of 'Sunbelki'.
3. Plants of the new *Calibrachoa* were more freely branching than plants of 'Sunbelki'.
4. Plants of the new *Calibrachoa* had lighter yellow-colored flowers than plants of 'Sunbelki'.

BRIEF DESCRIPTION OF THE PHOTOGRAPHS

The accompanying colored photographs illustrate the overall appearance of the new *Calibrachoa,* showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of a typical flowering plant of 'Sunbelremo' grown in a container.

The photograph at the bottom of the sheet is a close-up view of a typical flower and flower bud of 'Sunbelremo'.

DETAILED BOTANICAL DESCRIPTION

The aforementioned photographs and following observations, measurements and values describe plants grown in Higashiomi, Shiga, Japan, under commercial practice during the late spring in an outdoor nursery. During the production of the plants, day temperatures averaged 23° C. and night temperatures averaged 13° C. Plants had been growing for four and five months when the description and photographs, respectively, were taken. In the following description, color references are made to The Royal Horticultural Society Colour Chart, 2001 Edition, except where general terms of ordinary dictionary significance are used.

Botanical classification: *Calibrachoa* sp. 'Sunbelremo'.

Parentage:

*Female, or seed, parent.*—Proprietary selection of *Calibrachoa* sp. identified as code number S39, not patented.

*Male, or pollen, parent.*—Proprietary selection of *Calibrachoa* sp. identified as code number YS5, not patented.

Propagation:

*Type.*—By vegetative cuttings.

*Time to initiate roots.*—About one week at 15° C. to 20° C.

*Time to produce a rooted young plant.*—About three weeks at 15° C. to 20° C.

*Root description.*—Fibrous; white in color.

*Rooting habit.*—Freely branching.

Plant description:

*Plant and growth habit.*—Upright and mounding plant habit. Freely branching habit with numerous lateral branches developing per plant; pinching is not required, but will enhance lateral branch development; vigorous growth habit.

*Plant height.*—About 25 cm.

*Plant diameter.*—About 43.4 cm.

Lateral branch description:

*Length.*—About 25.9 cm.

*Diameter.*—About 2 mm.

*Internode length.*—About 1.5 cm.

*Strength.*—Strong.

*Aspect.*—Upright to outward.

*Texture.*—Pubescent.

*Color.*—Close to 144A.

Foliage description:

*Arrangement.*—Alternate, simple.

*Length.*—About 3.2 cm.

*Width.*—About 1.2 cm.

*Shape.*—Narrowly elliptic.

*Apex.*—Broadly acute.

*Base.*—Cuneate.

*Margin.*—Entire.

*Texture, upper and lower surfaces.*—Pubescent.

*Venation pattern.*—Pinnate; reticulate.

*Color.*—Developing and fully expanded leaves, upper surface: Close to 137B; venation, close to 145B. Developing and fully expanded leaves, lower surface: Close to 138B; venation, close to 145B.

*Petiole.*—Length: About 3.6 mm. Diameter: About 1.3 mm. Texture, upper and lower surfaces: Sparsely pubescent. Color, upper and lower surfaces: Close to 145B.

Flower description:

*Flower arrangement and habit.*—Single salverform flowers arising from upper leaf axils. Freely flowering habit with usually about 62 open flowers per plant at one time. Flowers face upright or outwardly.

*Fragrance.*—Not detected.

*Natural flowering season.*—Plants of the new *Calibrachoa* initiate and develop flowers about three to four weeks after planting. Long flowering period; flowering commences naturally during the spring and plants flower continuously throughout the summer until late autumn in Japan.

*Flower longevity.*—Individual flowers last about seven to ten days on the plant; flowers not persistent.

*Flower diameter.*—About 3.3 cm.

*Flower length (depth).*—About 2.8 cm.

*Throat diameter.*—About 7.8 mm.

*Tube length.*—About 1.8 cm.

*Tube diameter.*—About 2 mm.

*Flower bud.*—Shape: Cylindrical. Length: About 2.2 cm. Diameter: About 8.3 mm. Color: Close to 150C.

*Corolla.*—Arrangement: Five petals fused at the base and opening into a flared trumpet. Petal length from throat: About 1.4 cm. Petal width: About 1.2 cm. Petal shape: Spatulate. Petal apex: Rounded to truncate; blunt. Petal margin: Entire. Petal texture, upper and lower surfaces: Smooth, glabrous. Throat texture: Smooth, glabrous. Tube texture: Pubescent. Color: Petal, when opening and fully open, upper surface: Close to 4D; venation, close to 7B. Petal, when opening and fully open, lower surface: Close to 4D; venation, close to 4D. Throat: Close to 7B; venation, close to 7B. Tube: Close to 1B; venation, close to 1B.

*Calyx.*—Arrangement: One star-shaped calyx tube with five sepals fused at the base. Sepal length: About 8.3 mm. Sepal width: About 2.8 mm. Sepal shape: Lanceolate. Sepal apex: Rounded. Sepal margin: Entire. Sepal texture, upper and lower surfaces: Pubescent.

Color, immature and mature, upper surface: Close to 137C. Color, immature and mature, lower surface: Close to 137D.

*Peduncles.*—Length: About 2.2 cm. Diameter: About 0.8 mm. Angle: Upright to outward. Strength: Strong. Texture: Pubescent. Color: Close to 144B.

*Reproductive organs.*—Stamens: Quantity/arrangement: Five per flower. Stamen length: About 1.1 cm. Anther shape: Ellipsoidal. Anther size: About 1.2 mm by 1.6 mm. Anther color: Close to 10D. Pollen amount: Moderate. Pollen color: Close to 10D. Pistils: Quantity: One per flower. Pistil length: About 9.3 mm. Style color: Close to 145B. Stigma shape: Transversely ellipsoidal. Stigma color: Close to N144C. Ovary color: Close to 145A. Seed/fruit: Seed and fruit development have not been observed on plants of the new *Calibrachoa.*

Garden performance: Plants of the new *Calibrachoa* have been observed to have good garden performance and to tolerate wind, rain and temperatures ranging from about 5° C. to about 35° C.

Pathogen/pest resistance: Plants of the new *Calibrachoa* have not been observed to be resistant to pests and pathogens common to *Calibrachoa.*

It is claimed:

1. A new and distinct *Calibrachoa* plant named 'Sunbelremo' as illustrated and described.

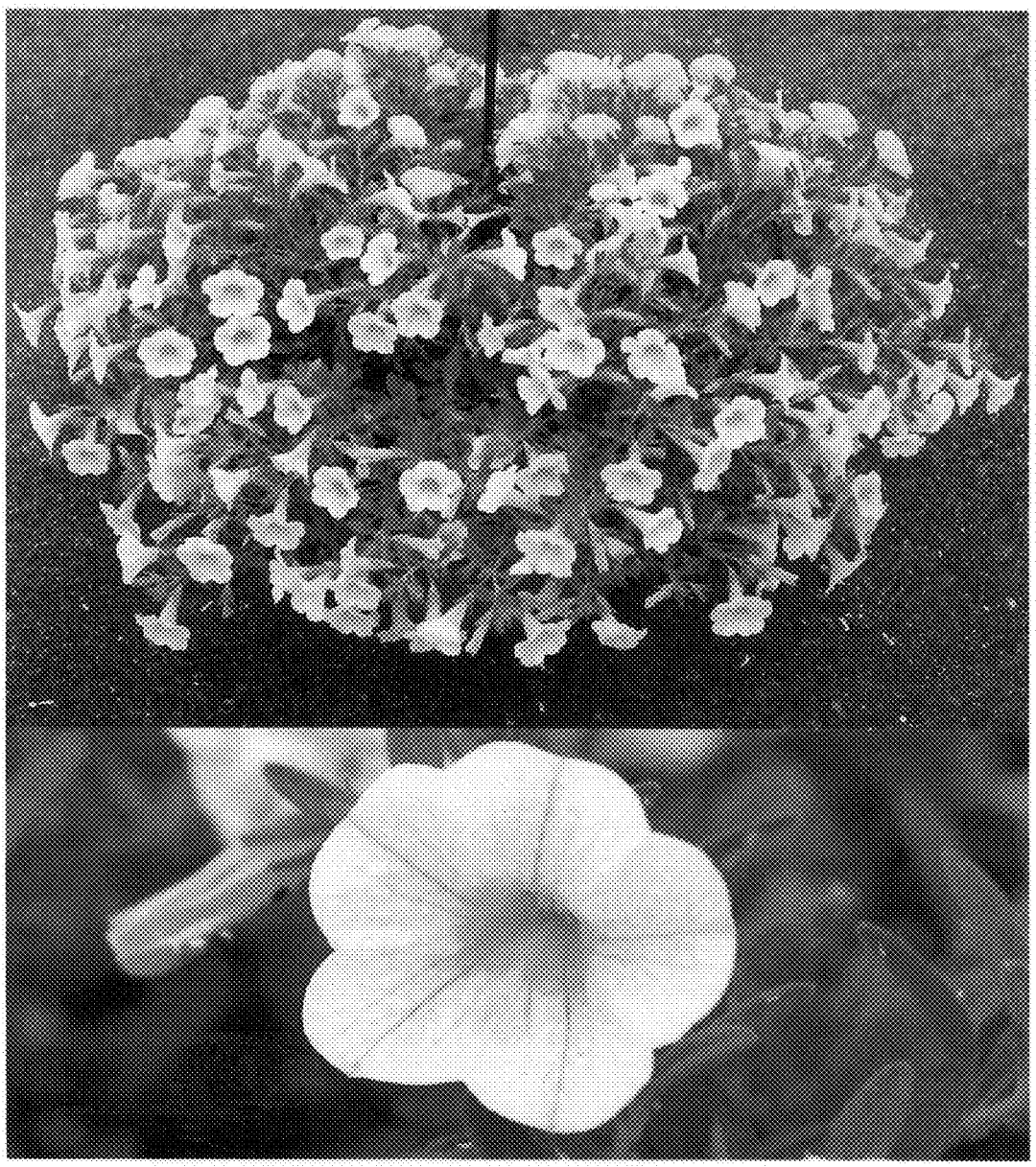

* * * * *